United States Patent [19]

Averill et al.

[11] Patent Number: 5,443,519
[45] Date of Patent: Aug. 22, 1995

[54] PROSTHETIC ELLIPSOIDAL ACETABULAR CUP

[75] Inventors: Robert G. Averill, Ringwood; Robert C. Cohen, Rockaway Township, both of N.J.

[73] Assignee: Implex Corporation, Allendale, N.J.

[21] Appl. No.: 52,248

[22] Filed: Apr. 22, 1993

[51] Int. Cl.⁶ .................................................. A61F 2/34
[52] U.S. Cl. ................................. 623/22; 623/18
[58] Field of Search ........................... 623/18, 22, 23

[56] References Cited

U.S. PATENT DOCUMENTS

| | | |
|---|---|---|
| D. 296,714 | 7/1988 | Averill et al. |
| 4,623,352 | 11/1986 | Oh. |
| 4,662,891 | 5/1987 | Noiles. |
| 4,695,282 | 9/1987 | Forte et al. |
| 4,704,127 | 11/1987 | Averill et al. |
| 4,715,859 | 12/1987 | Schelhas et al. |
| 4,770,660 | 9/1988 | Averill. |
| 4,778,474 | 10/1988 | Homsy. |
| 4,795,470 | 1/1989 | Goymann et al. |
| 4,871,368 | 10/1989 | Wagner. |
| 4,878,916 | 11/1989 | Rhetner et al. |
| 4,883,490 | 11/1989 | Oh ............................... 623/22 |
| 4,883,491 | 11/1989 | Mallory et al. |
| 4,892,549 | 1/1990 | Figgie, III et al. |
| 4,936,861 | 6/1990 | Muller et al. |
| 4,955,917 | 9/1990 | Karpf. |
| 4,963,154 | 10/1990 | Anapliotis. |
| 5,092,897 | 3/1992 | Forte. |
| 5,108,447 | 4/1992 | Zeiler et al. |
| 5,192,329 | 3/1993 | Christie et al. ............... 623/22 |

FOREIGN PATENT DOCUMENTS

| | | | |
|---|---|---|---|
| 2626168 | 7/1989 | France | 623/22 |
| 2805305 | 8/1978 | Germany | 623/22 |
| 3341723 | 3/1985 | Germany | 623/22 |

*Primary Examiner*—David Isabella
*Attorney, Agent, or Firm*—Arthur L. Plevy

[57] ABSTRACT

An acetabular cup prosthetic device comprised of an outer shell component and a inner bearing insert and the method of implanting the acetabular cup prosthetic within a patient. The outer surface of the shell component for the present invention acetabular cup has a plurality of regions which conform to the curvature of at least one ellipsoid. To implant the shell component, the acetabulum of a patient is spherically reamed to a size slightly smaller than that of the outer surface of the shell component. As the shell component is inserted into the spherically shaped acetabulum, the interior surface of the acetabular cavity deforms to assume a substantially ellipsoidal curvature, producing an interference fit between the rim region of the shell component and the upper peripheral rim region of the acetabulum. The remaining surface regions of the acetabulum conform substantially to the ellipsoidal shape or shapes defined by the remaining surface regions of the shell component so that surface contact is established without the development of ejection forces therebetween.

15 Claims, 11 Drawing Sheets

PROSTHETIC ELLIPSOIDAL ACETABULAR CUP

FIELD OF THE INVENTION

The present invention relates to an acetabular cup prosthesis for use in a total hip joint replacement procedure and more particularly to acetabular cups and associated items which provide improved function.

BACKGROUND OF THE INVENTION

The human hip joint acts mechanically as a ball and socket joint, wherein the ball-shaped head of the femur is positioned within the socket-shaped acetabulum of the pelvis. In a total hip joint replacement, both the femoral head and the surface of the acetabulum are replaced with prosthetic devices. One of the critical concerns in a total hip joint replacement procedure is how to achieve a strong attachment between the prosthetic devices and the patient's bone, both at the time of the implantation and throughout the life of the prosthesis. The problem of anchoring the prosthetic devices to a patient's bone is of a particular concern with an acetabular cup prosthesis. Many conventional acetabular cup devices are hemispherical cups which are secured within a prepared acetabulum either with an interference fit, mechanical attachment devices and/or adhesive attachment materials such as bone cement.

The use of bone cement in attaching an acetabular cup prosthesis within an acetabulum provides an excellent immediate attachment but has various disadvantages that appear over time. Load stresses are repeatedly applied to the acetabular cup over the life of the prosthesis. If bone cement is used to secure the cup to the acetabulum, the bone cement may fatigue and fracture under the repeated loading. In some instances, degradation of the bone cement integrity may cause the cup to become loose, thereby necessitating replacement. Additionally, in applying bone cement within a patient's acetabulum, anchoring holes are typically drilled into surrounding bone to provide anchoring points for the bone cement. If the bone cement were to fracture and the cup require replacement, the old bone cement must be removed from the anchoring holes in the bone. Such a procedure is complex, time consuming and potentially destructive to healthy bone structures surrounding the acetabulum. Furthermore, conventional bone cement is cured after it has been dispensed into the patient's acetabulum. Chemical releases occur from the bone cement as the cement is placed and cured within the acetabulum. Such releases may cause adverse reactions in some patients and increases the risks incurred by the patient receiving the hip joint replacement procedure.

Recognizing the disadvantages of cement fixation techniques, prior art acetabular cups have been developed that utilize mechanical attachment means, to join the cup to the acetabulum for immediate stabilization, and various surface treatments intended to bond with bone biologically for long term stable attachment. A simple technique of mechanically securing an acetabular cup, is to affix the cup within the acetabulum with screws or other mechanical fasteners. However, due to the nature of the bone surrounding the acetabulum, and other limiting factors such as artery location and the like, screws can only be applied in certain limited regions. Further, although screws can provide supplemental attachment and stabilization of the cup, they can be used to stably attach a cup where the geometry of the cup is poorly matched to that of the prepared acetabulum.

Another method of mechanically securing an acetabular cup is by the use of threads located on the exterior of the cup. In such an embodiment, the cup is rotated and pushed into the bone of the acetabulum where the teeth of the threads cut into, and engage, the bone. Such a method of implanting an acetabular cup into a patient is exemplified in U.S. Pat. No. 4,662,891 to Noiles, entitled FIXATION ELEMENTS FOR ARTIFICIAL JOINTS. Many prior art cups with threaded exterior surfaces, utilize relatively large threads with sharp points. A disadvantage of such prior art cups is that in the absence of biological attachment between the cup's outer surface and the bone, loading stresses applied to the cup are transferred largely to the threads. Since the periphery of the threads is generally sharp, large stress concentration points are created in the bone in the peripheral region of the threads. Such loading stresses may exceed the amount of stress that can be tolerated by the bone and produce adverse reactions within the bone, which, in some instances results in failure due to cup migration, loosening, pain, and/or joint dislocations.

An alternative method of implanting an acetabular cup involves the use of an interference fit as a means of initial stabilization. Certain prior art devices implanted with an interference fit, employ cups with hemispherical exterior surfaces. The acetabulum is spherically reamed to a given size and an oversized spherical cup is forcibly inserted to provide an interference fit. Spherical reaming of the acetabulum is preferred over other shapes because of its simplicity and ability to be more exactly reproduced from patient to patient. Referring to FIGS. 1a and 1b, a prior art hemispherical acetabular cup 110 is shown in conjunction with a prepared acetabulum 112. The hemispherical acetabular cup 110 has a known radius of curvature. The acetabulum 112 is spherically reamed to a radius of curvature slightly smaller than that of the cup 110. Consequently, the cup 110 can be implanted into the acetabulum 112 with an interference fit. In FIG. 1b, it can be seen that as the cup 110 is driven into the acetabulum 112, the acetabulum 112 is deformed. Only the forces applied by the deformed acetabular surface to the peripheral rim region of the cup 110 have a horizontal holding component which acts to frictionally retain the cup 110 within the acetabulum 112, thereby providing the interference fit. As can be seen in FIG. 1b, the deformation of the acetabulum results in a gap 113 between a surface region of the cup and of the acetabulum. No forces are applied to those portions of the cup 110 surrounded by the gap 113. Below the gap, however, the cup 110 once again engages the surface of the acetabulum, this time at the most apical region, where the vertical reactive forces imparted to the cup thereby tend to produce a bounce back effect that may prevent the cup 110 from being fully seated.

Other prior art acetabular cups have been developed that control the region of interference between the cup and the acetabulum, produced by an interference fit implantation. Referring to FIGS. 2a and 2b, a cup 114 is shown that has an external surface with two radii of curvature. The region 115 proximate the rim of the cup 114 has a larger radius of curvature than does the apical region 116 of the cup 114. The cup 114 is conventionally inserted into an acetabulum 117 that has been reamed to a radius of curvature approximately equal to the apical region 116 of the cup 114. When the cup 114 is fit within the acetabulum 117, the region 115 proximate the rim of the cup 114 displaces the acetabulum 117 and creates an interference fit. The displacement of the acetabulum 117 by the cup 114 causes the acetabulum 117 to deform away from its original spherically reamed shape. Consequently, the bottom of the reamed acetabulum is no longer spherically shaped as it is contacted by the apical region 116 of the cup 114. As can be seen from FIG. 2b, the spherically curved apical region 116 of the cup 114 does not perfectly conform to the non-spherical bottom of the acetabulum 117. Consequently, grooves 118 may exist along the cup-to-bone interface. A prior art cup embodying a dual-radius as described is exemplified in U.S. Pat. No. 4,892,549 to Figgie, et al., entitled DUAL-RADIUS ACETABULAR CUP COMPONENT.

In FIGS. 3a and 3b, a different prior art embodiment is shown wherein the acetabular cup 120 has a spherically curved apical region 121 and a frustrum-shaped rim region 122. The difference in shapes between the rim region 122 and the apical region 121 is pronounced, providing the cup 120 with a stepped exterior surface. To accommodate the cup 120, the acetabulum 124 must be reamed with two differently sized and shaped reamers so that the acetabulum 124 can properly accommodate the stepped exterior of the cup 120. The required two stepped reaming operation of acetabulum 124 increases the complexity and labor required in implanting the cup 120. As the cup 120 is fit within the reamed acetabulum 124, the rim region 122 of the cup 120 displaces the acetabulum 124 so as to create an interference fit between the cup rim region 122 and the acetabulum 124. The acetabulum 124 is originally reamed to be spherical. However, the displacement of the acetabulum 124 caused by the rim region 122 of the cup 120, causes the acetabulum 124 to distort away from its original spherical shape. Consequently, the spherically shaped apical region 121 of the cup 120 does not lay flush against the acetabulum 124. As such, grooves 125 may occur along the cup-to-bone interface at various positions across the apical region 121 of the cup 120. A prior art cup embodying the cup geometry as above-described is exemplified in U.S. Pat. No. 4,704,127 to Averill, et al., entitled DUAL-GEOMETRY ACETABULAR CUP COMPONENT AND METHOD OF IMPLANT.

It is also noted that certain prior art acetabular cups are provided to the users as a two-part device, wherein an inner bearing insert is fitted to an outer shell by the practitioner. Employing a two-part device makes it possible to offer one series of outer shell sizes and to provide an array of inner bearing inserts for subsequent assembly that accommodate differently sized femoral heads. A two-part construction also allows the femoral head to contact a material that provides less friction to the femoral head than would the material of the shell. Such a two-part cup prosthesis is exemplified by U.S. Pat. No. 4,795,470 to Goymann et al., entitled, TWO-PART SOCKET FOR HIP-JOINT PROSTHESIS.

It is known that when a patient with a hip joint replacement implements motions of that limb, the head of the femoral prosthesis will transmit forces to the cup in varying directions and that the neck of the femoral prosthesis may occasionally contact the rim of the implanted cup. As a result of such varying forces and/or contact, forces occur which attempt to move the cup relative to the acetabulum in various ways. In the two piece cup described above, these same complex forces act on the inner bearing and attempt to rock, rotate and translate the inner bearing insert relative to the outer shell. A less than fully secured bearing insert would result in micro-motion between the bearing insert and the outer shell. Such micro-motion may cause wear of the bearing insert which further detracts from the integrity of the insert-to-shell interface. To prevent the disassociation of the insert from the shell, various methods of retaining the bearing insert within the outer shell have been developed. For example, certain prior art devices have a keyed projection formed on the outer surface of the bearing insert. The keyed projection fits within an aperture, formed through the outer shell, to assure the general apical alignment of the bearing insert relative to the outer shell, but like other commercialized methods of retention, does not prevent micro-motion between shell and insert. Such prior art prosthetic devices are exemplified by U.S. Pat. No. 4,878,916 to Rhenter et al., entitled PROSTHETIC CUP.

Another common prior art method of affixing a bearing insert within a shell component is by using screws or other mechanical fasteners, as exemplified by U.S. Pat. No. 5,092,897 to Forte, entitled IMPLANTABLE ACETABULAR PROSTHETIC HIP JOINT WITH UNIVERSAL ADJUSTABILITY. This construction provides security against the macro-motion of the acetabular cup within the acetabulum but generally does not prevent the micro-motion that occurs at the screw head to shell interface or at the insert-to-shell interface.

Another prior art method of retaining a bearing insert within the shell component is by using a snap-fit configuration. Such mechanisms have addressed, to varying degrees, the potential for disassociation of the insert from the shell but do not address the potential for micro-motion and the resulting adverse affects of wear debris.

Two part acetabular cups are intended to be assembled at the time of surgery for the convenience of insert size selection and outer shell insertion. This manual assembly during surgery requires that the manufacturers insure the long term interchangeability of parts, which in turn leads to dimensional tolerances that produce clearances between the two components in most, if not all assemblies. These designed clearances result in an unavoidable potential for micro-motion existing between the insert and the shell when exposed to the complex and cyclic loads that are predictably experienced by the hip joint. Furthermore, these clearances between the parts constitute void spaces that fill with body fluids and mix with the wear debris that result from micro-motion. Since the loads being transmitted across the two parts are both cyclic and varied in direction, the void spaces open and close in a pistoning fashion causing the contained mixture of body fluids and wear debris to be expressed. If apertures exist in the shell in the form of screw holes or other apertures, the debris laden fluids may be expressed into the interface between the shell and the acetabulum where fixation between the shell and the bone is intended. The injection of wear debris into the bone is clearly undesirable in light of the fact the wear debris is thought to cause bone lysis which in turn may lead to loosening of the cup and the need for reoperation with reduced probability of an enduring reconstruction.

In view of the above, there is described an improved acetabular cup that can be implanted with an interference fit and is operative to avoid many of the above-noted prior art problems relating to the fit and stability of the cup. There is further described an improved shell component and bearing insert that is preassembled in a manner that substantially eliminates both micro-motion and voids between the shell component and the bearing insert.

SUMMARY OF THE INVENTION

The present invention is an acetabular cup prosthetic device comprised of an outer shell component that includes a cavity for accommodating an inner bearing insert, and a method of implanting the acetabular cup within the acetabulum of a patient.

The shell component of the acetabular cup has an outer surface that is implanted within the acetabulum of a patient. The outer surface is comprised of a plurality of regions wherein all surface regions follow the curvature of one or more ellipsoids. To implant the shell component within the acetabulum of a patient, the acetabulum is spherically reamed to a define a volume which is slightly smaller than the volume circumscribed by the outer surface of the shell component. As the shell component is inserted into the spherically reamed acetabulum, the acetabulum distorts to a shape that generally conforms to an ellipsoid. Consequently, as the shell component is inserted into a patient's acetabulum, the shape of the acetabulum is deformed to accommodate the outer contour of the shell component so that the acetabular wall contacts substantially all outer surface portions along the contour thereof while interference forces develop only in the peripheral rim region.

Annular locking ribs and locking grooves are formed on the outer surface of the shell component in the region proximate the rim. The locking ribs displace the bone forming and surrounding the acetabulum as the shell component is implanted into a patient. The locking ribs mechanically engage the bone, joining the shell component to the acetabulum. The locking grooves have generally upwardly converging sidewalls and accordingly have a dovetail-shaped cross-sectional profile. When the shell component is implanted into the acetabulum, bone grows into the locking grooves. The dovetail shape of the locking grooves causes the ingrown bone and the shell component to become dimensionally interlocked. The mechanical forces joining the shell component to the acetabulum, created by the interference fit and the presence of the locking ribs, holds the shell component into a set position within the acetabulum and resists the various forces that act in the immediate and the long term to displace the shell component of the prosthesis. Over the long term, the grooves located between the locking ribs will also resist displacement of the shell component relative to the acetabulum by enabling the ingrowth of bone therebetween.

A bearing insert is retained within an accommodating cavity in the shell component of the cup, via an interference fit. The shape of the bearing insert corresponds to the shape of the cavity formed within the shell component. As such, the creation of the interference fit substantially eliminates voids between the shell component and the bearing insert across the various surfaces of the shell component and bearing insert in abutment. The bearing insert and shell component also include oppositely inclined surfaces that create a wedged condition between the bearing insert and the shell component. The wedge condition operates to seat the bearing insert within the shell component and prevents the potential of pistoning of the bearing insert and removal of the bearing insert from the shell component.

BRIEF DESCRIPTION OF THE DRAWINGS

For a better understanding of the present invention, reference is made to the following descriptions of exemplary embodiments thereof, considered in conjunction with the accompanying drawings, in which.

DETAILED DESCRIPTION OF THE DRAWINGS

Figure 4:
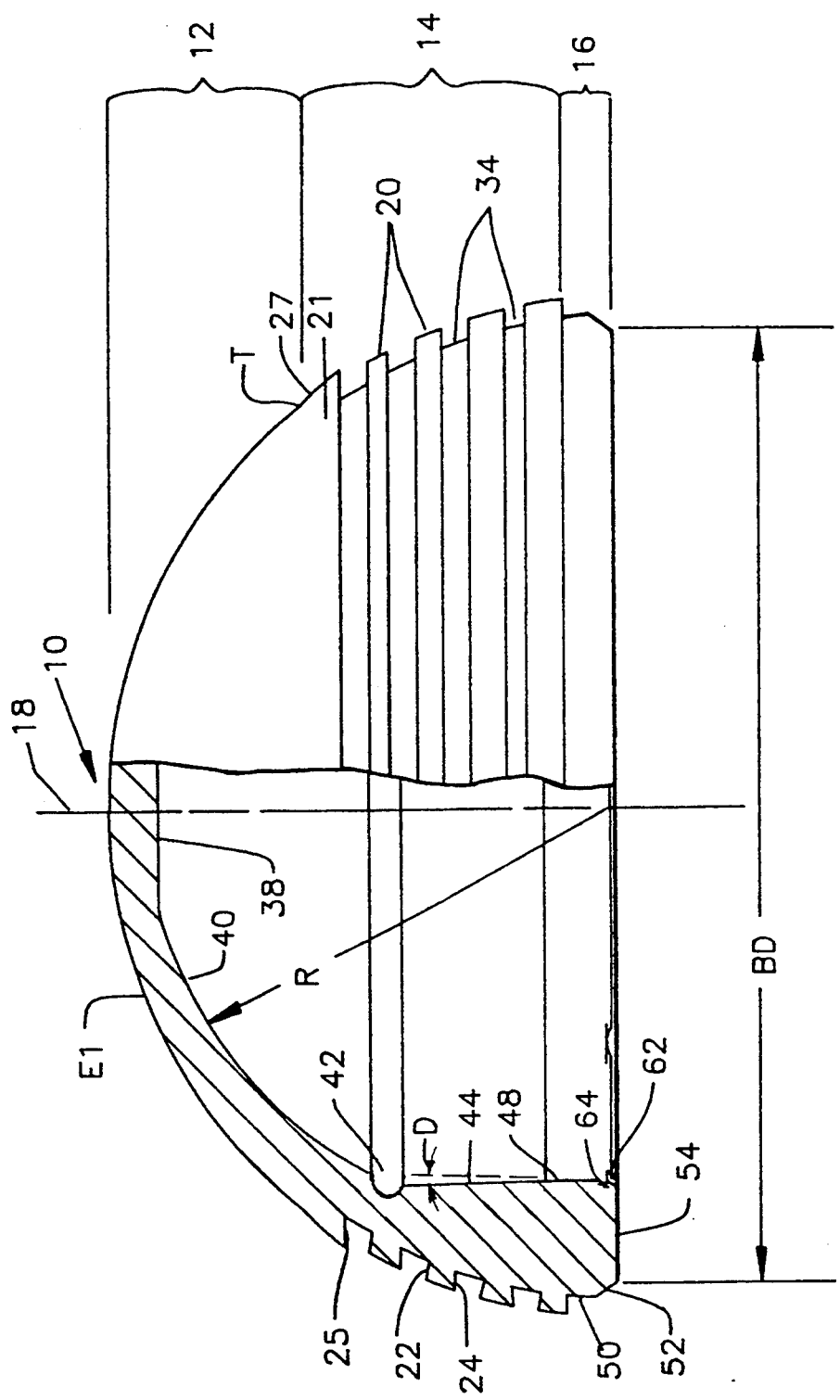
FIG. 4 is a partially cross-sectioned view of one preferred embodiment of the shell component of the present invention.

In FIG. 4, there is shown a partially cross-sectioned view of one preferred embodiment of the shell component 10 of the present invention acetabular cup prosthesis. The outer surface of the shell component 10 is contoured and is comprised of an apical region 12, a rim region 14 and a small base region 16. The surface curvature of the apical region 12 is ellipsoidal having a cross-sectional surface curvature that generally follows an elliptical curve E1. The minor axis of the elliptical curve E1 is determined along mid-axis line 18 while the major axis of the elliptical curve E1 is determined at a perpendicular to the mid-axis line 18, within the plane of the paper. In the preferred embodiment of the shell component 10, the major axis of the elliptical curve E1 is between 0.5 millimeters to 4.0 millimeters larger than the minor axis of the elliptical curve E1, depending upon the size of the acetabulum into which the shell component 10 is to be implanted.

With continuing reference to FIG. 4, it can be seen that a plurality of locking ribs 20 are provided along the rim region 14 of the shell component 10. The locking ribs 20 are arranged in parallel rows and are coaxially positioned around the mid-axis 18 of the shell component 10. Furthermore, a transition rib 21 is disposed on the shell component 10 at the top of the rim region 14. The transition rib 21 is also arranged in parallel with the locking ribs 20 and is coaxially positioned around the mid-axis 18 of the shell components 10.

Figure 5B:
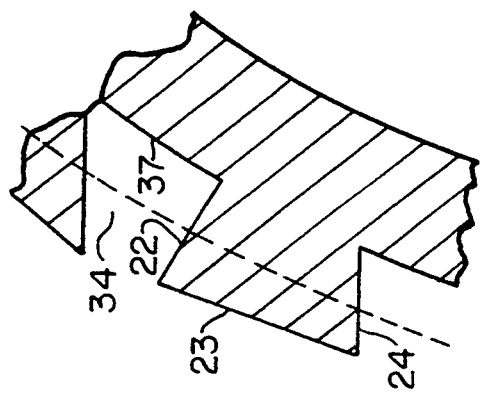
FIGS. 5a and 5b show enlarged segments of FIG. 4.
Figure 5A:
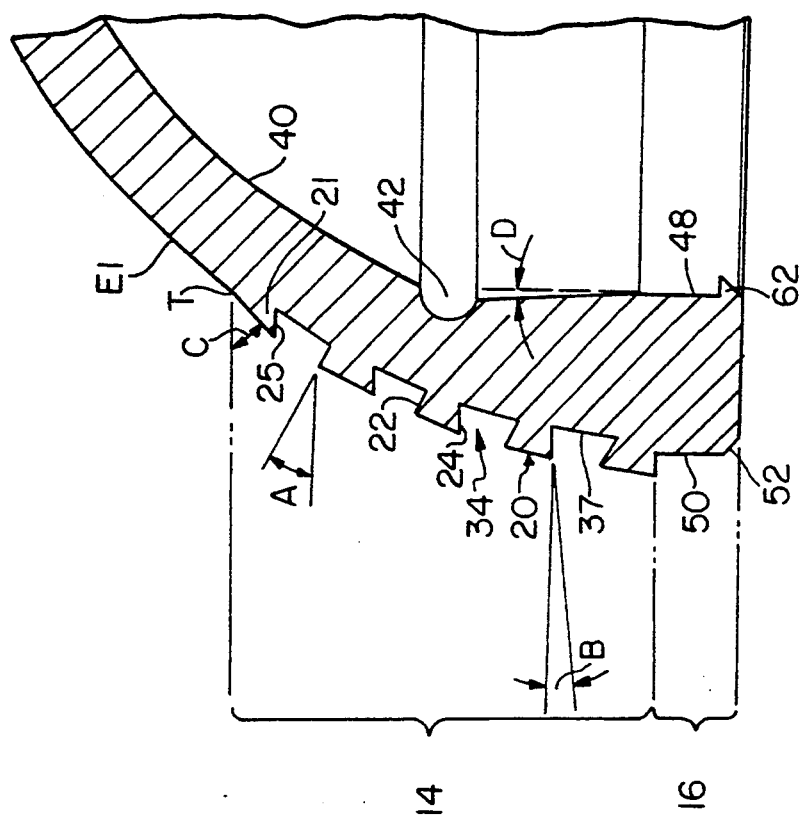

As more clearly shown in FIG. 5a, each of the locking ribs 20 may be provided with a generally dovetailed-shaped cross-sectional profile that includes first and second upwardly diverging sidewall surfaces, 22 and 24 respectively. In the illustrated embodiment, the first surface 22 of each locking rib 20 is inclined above the horizontal by a predetermined angle of inclination A. As such, the first surface 22 of each of the locking ribs 20 is parallel to the corresponding first surfaces of all the other locking ribs 20. Although the angle of inclination A, for each first surface 22 of each locking rib 20, can be any angle between 0° and 90°, in a preferred embodiment the angle of inclination A is approximately thirty degrees.

The second surface 24 of each locking rib 20 has a descending surface 24 that descends below the horizontal by a predetermined angle of declination B. Each second surface 24 is therefore parallel to the corresponding second surfaces of all the other locking ribs 20. Although the angle of declination B for each second surface 24 can be any angle between 0° and 90°, in a preferred embodiment the angle of declination B is approximately five degrees.

The transition rib 21 has a descending surface 25 that is parallel to the second surfaces 24 of each of the locking ribs 20 and shares the same angle of declination B. The transition rib 21 has a linear top surface 27 that meets the ellipsoidally curved surface of the apical region 12 of the shell component 10 at transition point T. The linear top surface 27 descends below a horizontal plane passing through transition point T by an angle of inclination C. Although the angle of declination C can be any acute angle, in the preferred embodiment, the angle of declination C is approximately forty five degrees.

Since the transition rib 21 and the locking ribs 20 are all disposed in parallel planes, grooves 34 are present between the transition rib 21 and the next adjacent locking rib 20, as well as between each of the locking ribs 20. In the illustrated embodiment, each groove 34 is defined on a first side by either the descending surface 25 of the transition rib 21 or the second surface 24 of a locking rib 20. The opposite side of each groove 34 is defined by the first surface 22 of an adjacent locking rib 20. As a result, each groove 34 is defined by upwardly diverging side walls that act to provide each groove 34 with a dove-tail-shaped cross-sectional profile.

As most clearly shown in FIG. 5b, locking ribs 20 preferably straddle elliptical curvature E1 so that the outer surface 23 of each rib 20 is disposed concentrically above the elliptical curvature E1. In like fashion, the base surface 37 of each groove 34 is disposed concentrically below the elliptical curvature E1. Alternatively, of course, the rib outer surfaces 23 and groove base surfaces 37 may be respectively contoured to extend above and below a second elliptical curvature (not shown) having major and minor axes which are different than those defined by elliptical curvature E1.

It will be readily appreciated that for ease of manufacture, the base 37 of each groove 34 may be flat and oriented to approximate the elliptical curvature E1. As will later be described, the geometry of the locking rings 20, as well as the dovetail-shaped profile of the grooves 34, allows bone ingrowth into the grooves 34 and enables the ingrown bone to mechanically engage the shell component 10.

Returning to FIG. 4, it can be seen that the base region 16 of the shell component 10 includes a substantially vertical surface 50 on the ellipse that extends below the second surface 24 of the lowermost locking rib 20 to chamfered edge 52. Chamfered edge 52 joins the substantially vertical surface 50 to the horizontal base surface 54 of the shell component 10.

Looking toward the interior surface of the cavity within the shell component 10, it can be seen that the apex region 38 of the interior surface is flat. Descending from the flat apex region 38 is a spherically curved surface 40 having a spherical radius R. The bottom of the spherically curved surface 40 terminates at an annular groove 42 formed into the shell component 10. Below the annular groove 42 descends an inclined engagement wall 44. The face of the inclined engagement wall 44 is angled slightly away from the vertical by a predetermined angle D. As such, it will be understood that the distance from the shell mid-axis 18 to the inclined engagement wall 44 increases as the inclined engagement wall 44 approaches the annular groove 42. Although the predetermined angle D can be any small acute angle, in the preferred embodiment the predetermined angle D should be approximately one degree from vertical. A vertical wall 48 descends from the bottom of the inclined engagement wall 44. The vertical wall 48 is parallel to the mid-axis 18 and does not show the slight inclination from vertical embodied by the inclined engagement wall 44. Locking projections 62 extend inwardly from the bottom of the vertical wall 48, proximate the base surface 54 of the shell component 10. Each of the locking projections 62 have a flat top surface 64 that extends inwardly, along the horizontal, from the vertical wall 48. The face surface of each locking projection 62 is sloped so as to match the bevel, present at the bottom of the vertical wall 48, that joins the vertical wall 48 to the base surface 54 of the shell component 10.

Figure 6A:
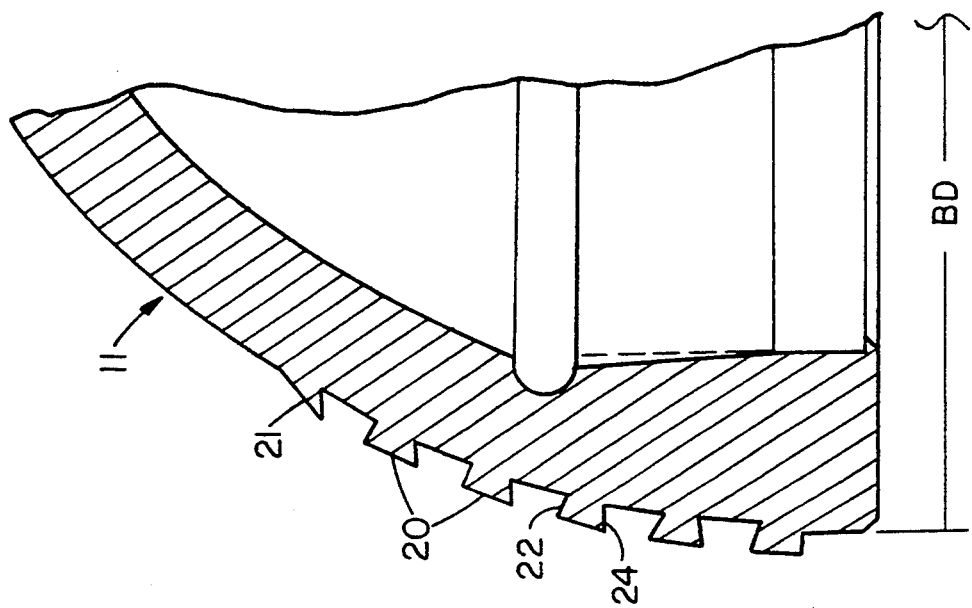
FIGS. 6a and 6b show segments of two alternate embodiments of the shell component, of the present invention.
Figure 6B:
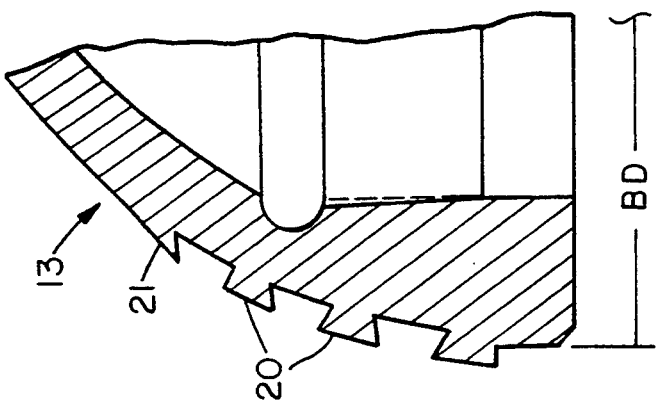

In the embodiment illustrated in FIGS. 4, 5a, and 5b, the shell component 10 has four locking ribs 20 and a transition rib 21. However, it will be understood that any plurality of locking ribs 20 may be used depending upon the size of the shell component 10 and the size and condition of the acetabulum into which the shell component 10 will be inserted. In FIG. 4, the shell component 10 is shown having a base diameter BD. In a preferred embodiment, the shell component 10 would have the shown four locking ribs 20, in addition to the transition 21, provided the base diameter BD were between 54 and 64 millimeters. Referring to FIG. 6a a cross-sectional segment of a shell component 11 is shown having five locking ribs 20 in addition to a single transition rib 21. Each of the five locking ribs 20 has the same ascending surface 22 and descending surfaces 24, as well as the same general orientation as has been previously described. The addition of a fifth locking rib is preferable in a larger size shell component. For example, the use of the shown five locking ribs 20 in addition to the transition rib 21 is preferable over the four locking rib design of FIG. 5, for shell components having a base diameter BD of between 66 and 70 millimeters. Similarly, if a smaller shell component were needed, less locking ribs would be needed. Referring to FIG. 6b, a cross-sectional segment of a shell component 13 is shown having three locking ribs 20 in addition to the single transition rib 21. The locking ribs 20 have the same general geometry as has been previously described but may be proportionately smaller depending upon the size of the shell component 13. The use of three locking ribs 20 in addition to a transition rib 21 is preferably used in conjunction with shell components 13 having a base diameter BD of between 40 and 52 millimeters.

Figure 7:
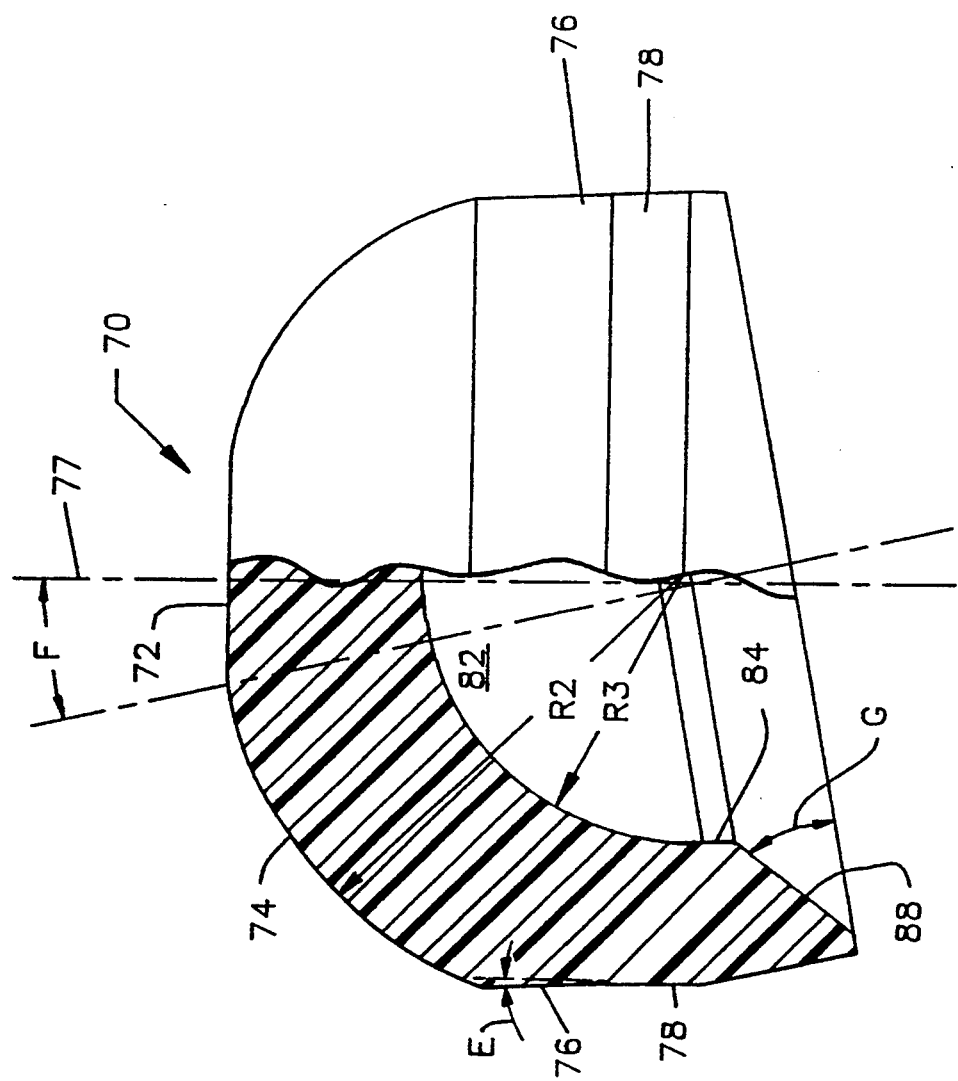
FIG. 7 is a partially cross-sectioned view of one preferred embodiment of the bearing insert component of the present invention.

In FIG. 7, one preferred embodiment of a plastic bearing insert 70 is shown, which is formed to fit within a previously described metal shell component. The top surface 72 of the bearing insert 70 is flat, having a dimensional area that corresponds to the inner flat apex region of a before described shell component. A spherically curved region 74 descends from the flat top region 72, wherein the curved region 74 has a radius R2. The radius R2 of the curved region 74 is generally equivalent to the inner surface radius present within the shell component. The bottom of the spherically curved region 74 terminates at a descending inclined surface 76. The inclined surface 76 is slightly askew from vertical, being off-set from the vertical by an angle of inclination E. As such, it will be understood that the distance from the bearing insert mid-axis 77 to the inclined surface 76 increases as the inclined surface 76 approaches the spherically curved region 74.

A vertical surface 78 extends downwardly from the bottom of the inclined surface 76. The vertical surface 78 is parallel to the bearing insert mid-axis 77 and does not share the slight inclination from vertical embodied by the inclined surface 76. In order to prevent pistoning of the bearing insert within the shell component, the nominal interior diameter or other cross sectional dimension of the shell component cavity is selected so that it is slightly smaller than the nominal exterior diameter or other cross sectional dimension of the bearing insert at room temperature. The specific tolerance will of course depend upon the thermal expansion properties of the materials used in fabricated the respective components. If the insert is constructed of sufficiently resilient plastic material, it may be press fit directly into the shell component. Of course, such a press fitting assembly can only be performed in a manufacturing environment utilizing mechanical devices capable of exerting the press forces required. Thus, before the bearing insert 70 can be inserted into the cavity of shell component 10 in a non-manufacturing environment, the maximum cross sectional area of the bearing insert must be rendered small enough for it to be admitted into the cavity without such equipment. For this purpose, the bearing insert 70 is preferably inserted cold within the shell component 10 by creating a temperature differential between the bearing insert 70 and the shell component 10 prior to insertion. When sufficiently cooled, the bearing insert 70 can be inserted into the shell component 10 without an interference. The temperature differential between the bearing insert 70 and the shell component 10 delays the interaction between the locking projections 62 that extend inwardly from the shell component 10 and the bearing insert 70 until the insert is fully seated therein. Cooling also permits the widest section of the bearing insert 70, as defined by the uppermost part of inclined surface 76, to clear the narrowest section of the cavity, as defined by the lowest portion of inclined surface 44. Once an equilibrium in temperature between the bearing insert 70 and the acetabular cup 10 has been established, an interference fit occurs across all surfaces in abutment. Furthermore, as a common temperature is reached and the interference created, the locking projections 62 embed themselves into the material of the bearing insert 70, enhancing locking of the bearing insert 10 into a set position relative the shell component 10.

The angle of inclination E of the inclined surface 76 is selected to increase the holding capabilities of the shell component 10 by keeping the insert 70 bottomed within the shell, thereby preventing pistoning. In a preferred embodiment, angle of inclination E is substantially complementary to the angle of inclination D (shown in FIGS. 4 and 5a) of the inclined engagement wall 44 on the interior surface of the shell component 10. As such, the preferred angle of inclination E is approximately one degree.

Because of the aforementioned relationship between the inclined engagement wall of the shell component 10 and the inclined surface 76 of the bearing insert 70, it should be appreciated that bearing insert 70 can not be readily positioned within (or removed from, as the case may be) the cavity of shell component 10.

A spherical cavity 82 having a radius R3 is formed within the bearing insert 70. The spherical cavity 82 is offset from the mid-axis 77 of the bearing insert 70 by an offset angle F. A short cylindrical wall 84 extends downwardly from the base of the spherical cavity 82. A beveled surface 88 is formed across the base surface 87 of the bearing insert 70, leading into the cavity 82. The beveled surface 88 has a angle of inclination G, which in a preferred embodiment is approximately thirty five degrees.

Figure 8:
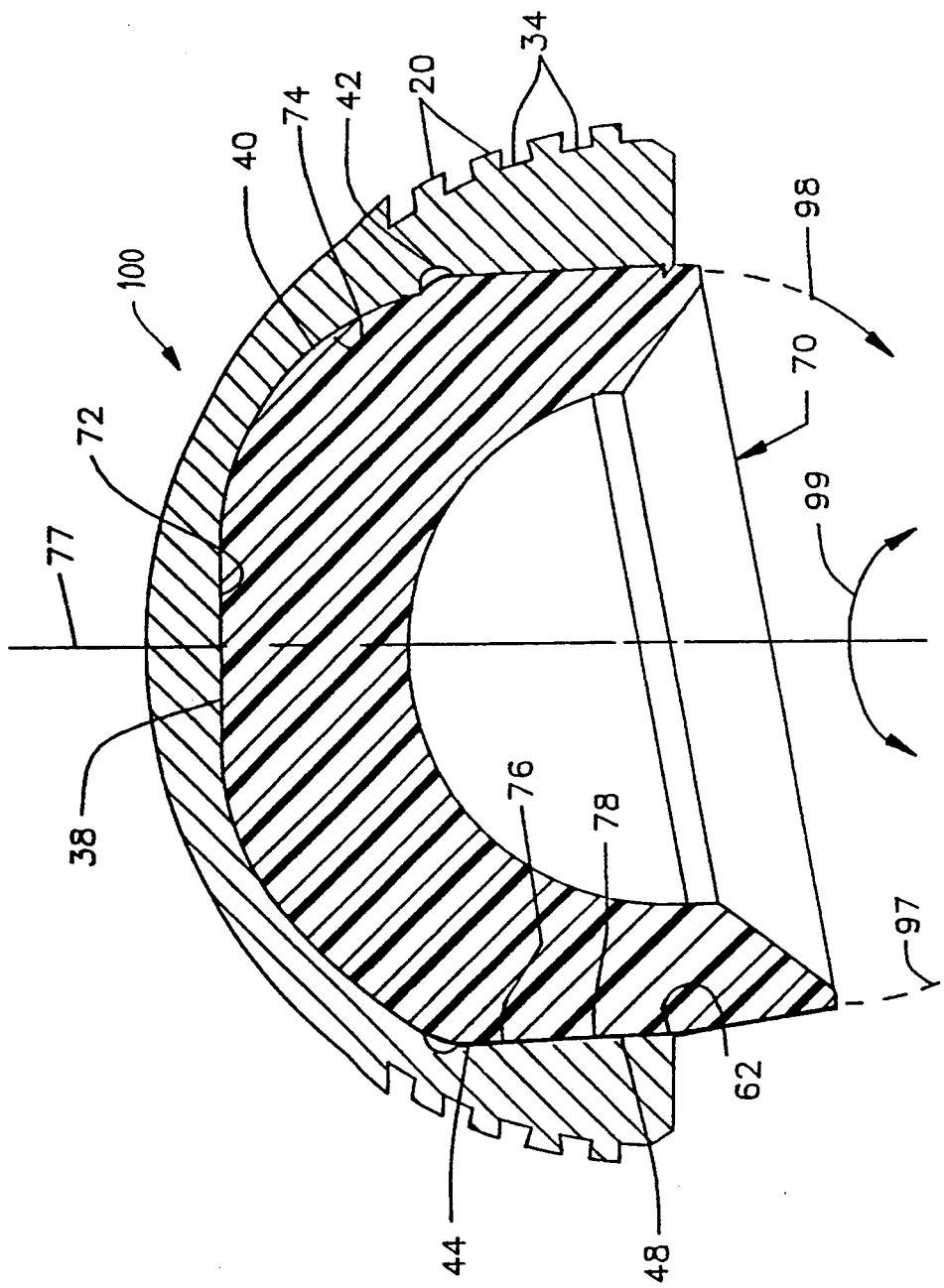
FIG. 8 is a cross-sectional view of one preferred embodiment of the present invention wherein the bearing insert of FIG. 7 is inserted into the shell component of FIG.4.

Referring to FIG. 8 the bearing insert 70, previously shown in FIG. 7, is shown joined to the shell component 10, previously shown in FIG. 4. At room temperature, the exterior surface of the bearing insert 70 generally conforms to the inner surface of the shell component 10. As such, the flat top region 72 of the bearing insert 70 lays flush against the flat apex region 32 within the shell component 10. Similarly, the spherically curved region 74 of the bearing insert 70 conforms to the spherically curved surface 40 within the shell component 10. The inclined surface 76 of the bearing insert 70 aligns against the inclined engagement wall 44 of the shell component 10. Since both the inclined surface 76 and the inclined engagement wall 44 are askew from the vertical by the same angle of inclination, both surfaces lay flush against each other across their respective lengths. Additionally, the vertical surface 78 of the bearing insert 70 aligns against the vertical wall 48 of shell component 10. Consequently, there exists contact across the exterior of the bearing insert 70 and the interior of the shell component 10, except in region of the annular groove 42, the purpose of which will be later explained. The interference between the bearing insert 70 and the shell component 10 substantially eliminates voids between the bearing insert 70 and the shell component 10, whereby the interference fit compensates for any tolerance variation that may exist between the bearing insert 70 and the shell component 10.

The interference fit between the bearing insert 70 and the shell component 10 extends across the abutment of the inclined engagement wall 44 with the similarly sloped inclined surface 76. Since both the inclined engagement wall 44 and the inclined surface 76 diverge from the vertical by the same amount, a wedge action is produced that maintains the seating of the bearing insert 70 within the shell component 10 and resists pistoning of the bearing insert 70 within the shell component 10, thereby preventing removal therefrom.

As a person undergoes certain movements, off-set loading may be experienced at the implanted acetabular cup. Such off-set loading may attempt to move the bearing insert 70 relative the surrounding shell component 10. Returning to FIG. 8, it can be seen that the rotational movement of the bearing insert 70 in directions of arrows 97, 98, or around the mid-axis 77, as indicated by arrow 99, is prevented by multiple components. First, the presence of the locking projections 62 cutting into the material of the bearing insert 70 prevents any such rotations. Moreover, the interference fit between the inclined surface 76 of the bearing insert 70 and the inclined wall 44 of the shell component 10, as enhanced by the resulting wedge action caused by the slight inclination of both surfaces, acts in combination with the interference fit between surfaces 78 and 48 to prevent any such rotation.

As discussed earlier, the attachment of the bearing insert 70 to the shell component 10 is done without the use of cement. Additionally, there exist no screw holes or other apertures in the shell component 10 that may permit any wear debris from the bearing insert 70 to pass through the shell component 10 and interfere with the regrowth of the bone or causes lysis. In certain instances, such as malposition or wearing in of the femoral head, the bearing insert 70 of an acetabular prosthesis 100 may need replacement. Since the surgeon can not conveniently employ the cold assembly technique used by the factory, the shell component 10 of the present invention is formed with an annular groove 42 on its interior surface above the inclined engagement wall 44. With the annular groove 42 in such an orientation, cement can be added in between the retained shell component 10 and in the region of the annular groove 42 of a new bearing insert designed for clearance assembly.

Figure 9:
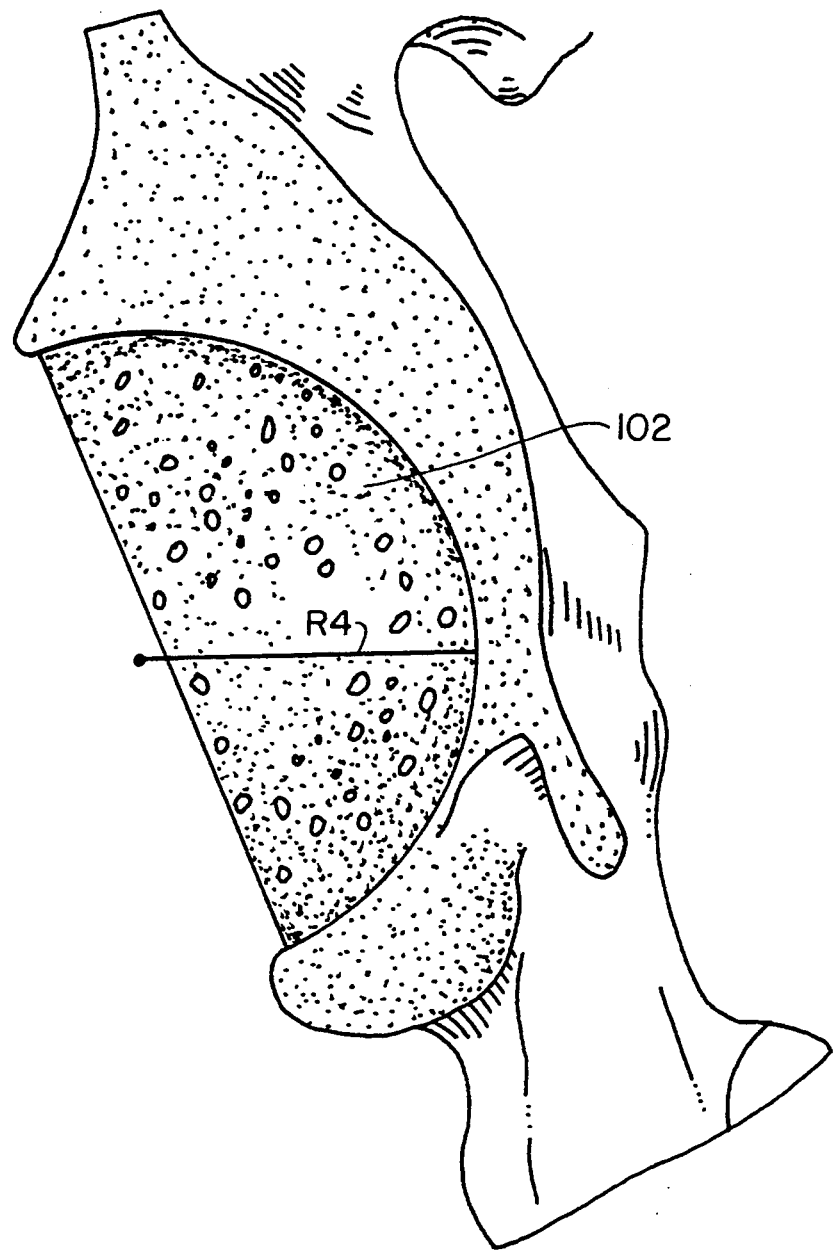
FIG. 9 is a selective cross-sectional view of a prepared acetabulum in a patient prior to the insertion of the present invention acetabular cup prosthesis.

Referring now to FIG. 9, the process of implanting the present invention acetabular cup 100 into an acetabular cavity 102 of a patient can be described. In FIG. 9, a cross-section of a patient's pelvis is shown in the area of a diseased or damaged acetabulum 102. The acetabulum 102 is then reamed into a spherical shape having a radius R4. The spherical reaming of an acetabulum 102 is a well practiced art and is conventionally performed with a spherically faced rotating reamer. The maximum cross sectional area measured transversely at the opening of the reamed acetabulum 102 is smaller than the maximum cross sectional area of the shell component 10 to be implanted (as transversely measured at base 16).

Figure 10:
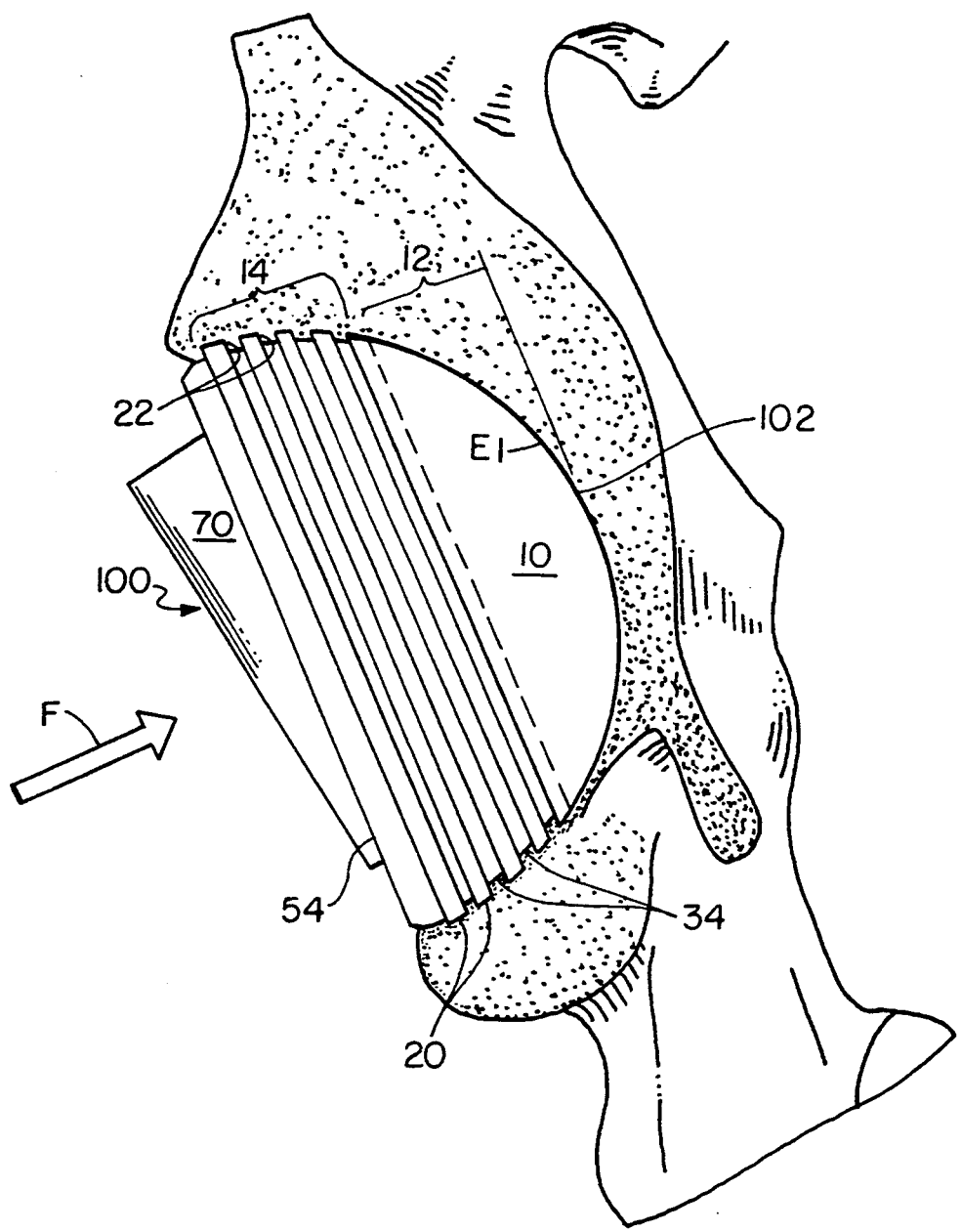
FIG. 10 is a selectively cross-sectioned view of the present invention acetabular cup prosthesis inserted into the prepared acetabulum of FIG. 9.

Referring to FIG. 10, the present invention acetabular cup prosthesis 100 is shown inserted into the spherically reamed acetabulum 102. The acetabular cup 100 is driven into the acetabulum 102 by impacting the acetabular cup 100 with a force F. Since the plastic bearing insert 70 is made of a material that is softer than the metal shell component 10, the force F needed to drive the acetabular cup 100 into the acetabulum 102 is preferably applied to the base surface 54 of the shell component 10 so not to cause the bearing insert 70 to deform. As the acetabular cup 100 is driven into the acetabulum 102, the locking ribs 20 on the exterior of the shell component 10 penetrate, to varying degrees, the bone in the region of the rim 103 of the acetabulum 102. The intended degree of locking rib penetration through local indentation of the bone and the scraping away of bone would place the original surface of the bone on the nominal ellipse E1. The angle of the ascending surface 22 of the various locking ribs 20 directs bone into the dovetail-shaped grooves 34 between adjacent locking ribs 20. Debris from the scraping action of the locking ribs 20 incurred during implantation is directed into the grooves 34, where it does not resist the further advancement of the acetabular cup 100 into the acetabulum 102. The grooves 34 are sufficiently wide to allow the eventual ingrowth of bone into the grooves 34. Thus, while the grooves 34 appear to be completely filled in with bone in FIG. 10, it will be readily appreciated that such complete ingrowth will only take place over an extended period of time and that immediately after implantation the only bone material in the grooves will be the aforementioned debris.

Prior to implantation, the maximum transverse cross sectional area of the spherically reamed acetabulum 102 is less than that of the shell component 10 being inserted. Moreover, the depth measured at the center of the reamed acetabulum 102 is greater than the depth of the shell component 10 at the most apical region (as measured along the minor axis of the shell component to its exterior surface). As such, when the shell component 10 is driven into the acetabulum 102, the peripheral rim region of the acetabulum 102 is stretched open.

Figure 1A:
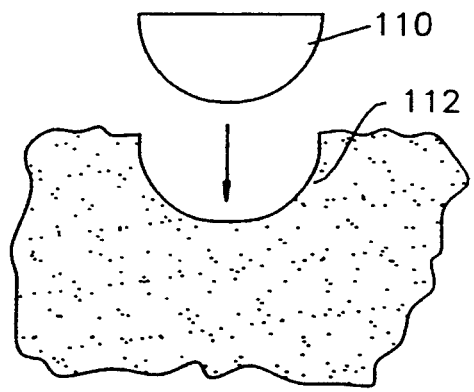
FIGS. 1a and 1b show a prior art hemispherical acetabular cup in conjunction with a spherically reamed acetabulum.
Figure 1B:
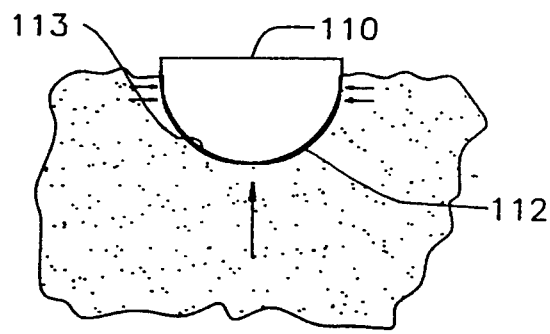
Figure 2A:
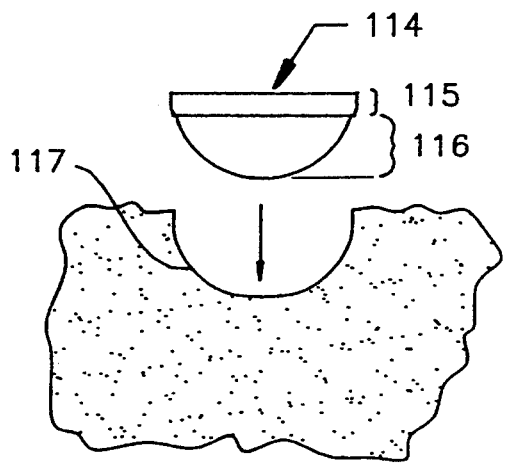
FIGS. 2a and 2b show a prior art dual-radius acetabular cup with a stepped exterior in conjunction with a spherically reamed acetabulum.
Figure 2B:
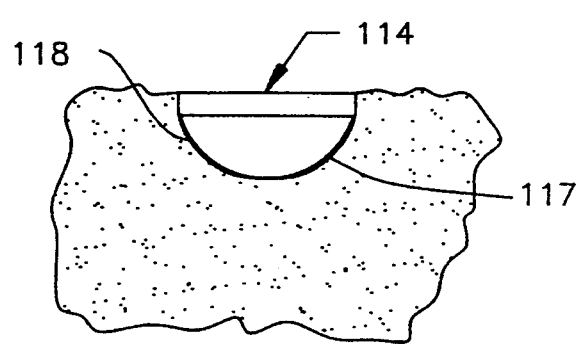
Figure 3A:
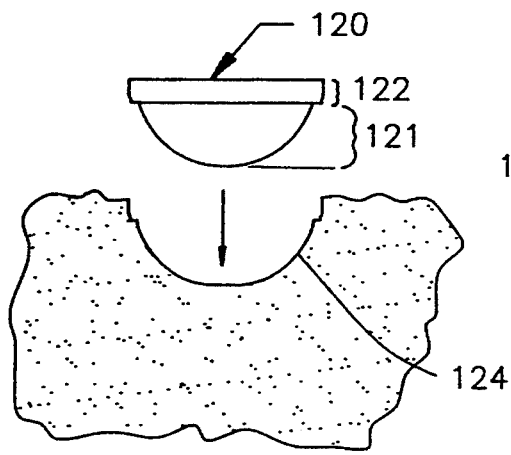
FIGS. 3a and 3b show a prior art acetabular cup with a stepped exterior in conjunction with an acetabulum reamed with separately shaped and sized reamers.
Figure 3B:
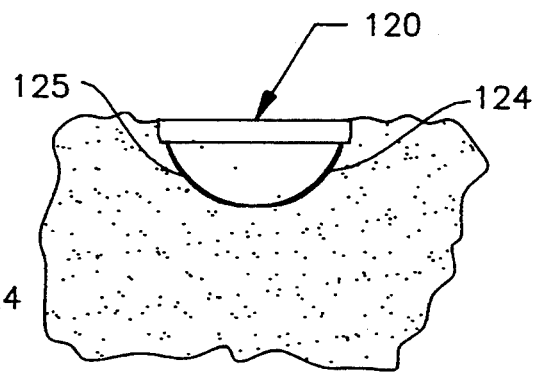

It should be readily appreciated by those of ordinary skill in the art that it is at the peripheral rim region where the greatest forces for producing the desired interference fit are developed. However, as most clearly shown in FIG. 1b, while the hemispherical shape of conventional acetabular cups capitalizes upon the forces generated at the peripheral rim region to produce an interference fit, it also results in the development of ejection forces at a region proximate the peripheral region and at the apical region. The inventors of the present invention have observed that the development of these ejection forces in the acetabulum predictably results from a corresponding deformation of the bone in the apical region which accompanies deformation of the rim region. Specifically, the curvature of the acetabulum 102 changes from that of a hemisphere to that of an ellipsoidal shape.

The ellipsoidal curvature of the implanted shell component 10 generally conforms to that of acetabulum 102 at the respective regions. As a result, minimal or no ejection forces are developed at the interface between the apical surfaces of the shell component and acetabulum. Advantageously, however, the same ellipsoidal curvature of the shell component provides the interaction of forces between the rim region 14 of the shell component 10 and the rim periphery of the acetabulum needed to produce the desired interference fit.

As noted above, since both the acetabulum 102 and the shell component 10 have corresponding ellipsoidal shapes, the acetabulum 102 engages the shell component 10 across the apical region 12 without applying ejection forces thereto so that the only forces created by the interference fit exist only at the rim region 14 of the shell component 10 and act to retain the shell component 10 within the acetabulum 102, Other advantages obtained by the present invention acetabular cup 100 is that by forcing the periphery of the acetabular cavity 102 to expand to the oversized major diameter ellipsoidal shape of the shell component 10, the resistance to movement of the shell component 10 to off-set loading is increased. Since both the shell component 10 and the acetabulum cavity 102 are non-spherical, the shell component 10 is less likely to rotate within the acetabulum cavity 102 and therefore provides greater resistance to movement caused by off-set loading.

Additionally, the elongation of the acetabulum cavity 102 by the insertion of the shell component 10 causes the bone to be biased against the shell component 10 as the bone tries to return to its spherically reamed shape. The bias of the bone causes the bone to press against the locking ribs 20 on the shell component 10, thereby driving the locking ribs 20 into the bone and causing bone to be biased into the dovetail-shaped grooves 34 in between each of the locking rings 20. Furthermore, the size of the grooves 34 allows the eventual ingrowth of the bone. As the bone grows within the grooves 34, the dovetail shape of the grooves 34 prevents the ingrown bone from being retracted from the between the locking ribs 20. The presence of the locking ribs 20 in the bone, and the presence of ingrown bone in the dovetail-shaped grooves 34, binds the shell component 10 to the bone, thereby resisting any movement of the shell component 10 caused by off-set loading or the variably sized and variably directed forces normally transferred across the joint.

Figure 11:
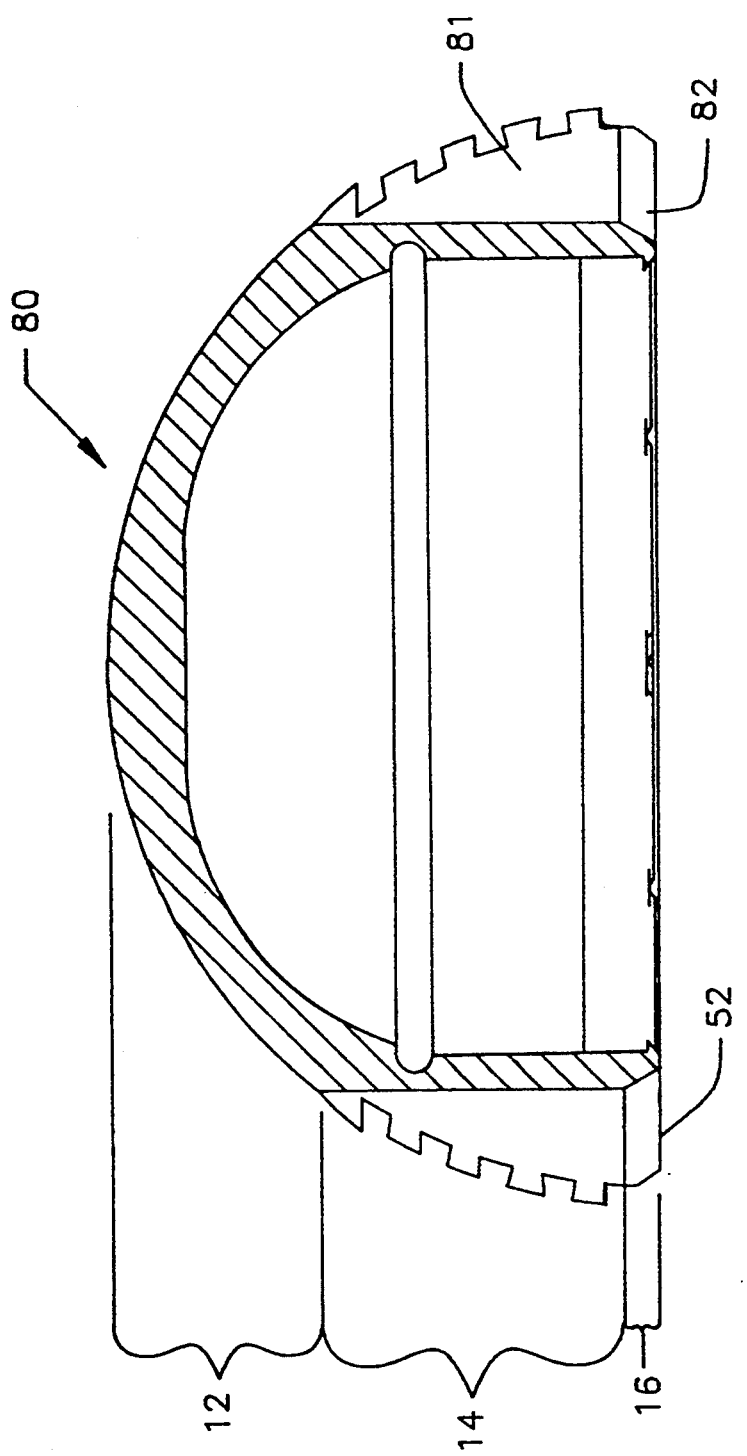
FIG. 11 is a cross-sectional view of an alternate embodiment of the shell component of the present invention.
Figure 12:
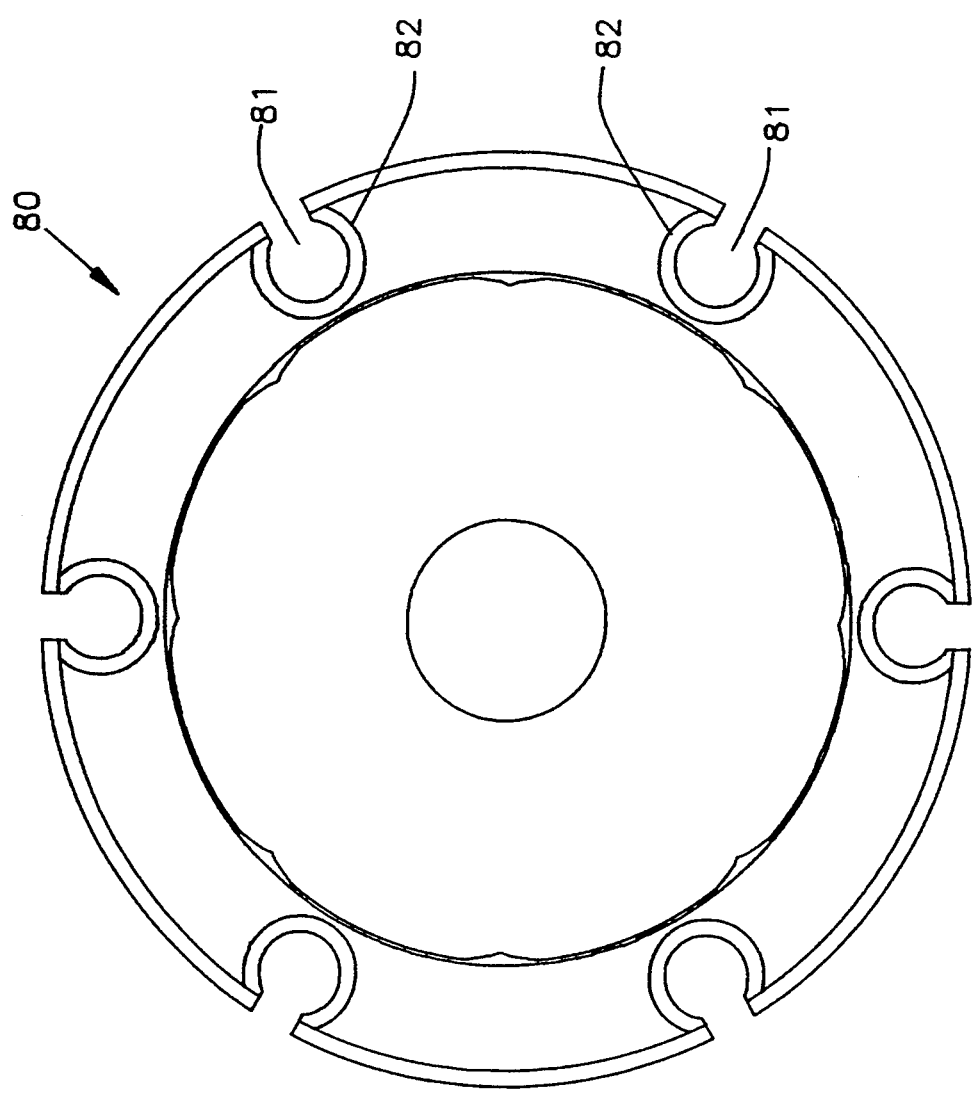
FIG. 12 is a bottom view of the shell component of FIG. 11.

Referring to FIGS. 11 and 12 an alternate embodiment of a shell component 80. The shown embodiment has the same shape as the embodiment previously described in connection with FIG. 4 except a plurality of screw holes 81 are now disposed through the shell component 80. The screw holes 81 extend through the rim region 14 and base region 16 of the shell component 80. The screw holes 81 do not intersect the apical region 12 of the shell component 80, as such the apical region 12 remains a solid ellipsoidal surface. The interior of the shell component 80 is unaffected by the presence of the screw holes 81. As a result, the interior surface of the shell component 80 is the same as has previously described and the shell component 80 engages a bearing insert in the same manner as has been previously described. Since the screw holes 81 do not intersect the interior surfaces of the shell component 80, the screw holes 81 do not provide a means for wear debris frown the shell/insert interface to travel to the exterior of the shell component 80. Consequently, the presence of the screw holes 81 do not increase the chances of wear debris escaping the shell component and causing lysis or otherwise causing adverse effects.

The screw holes 81 themselves are symmetrically disposed around the shell component 80. Although six screw holes 81 are shown, it will be understood that any number of screw holes 81 may be present, wherein the spacing between each of the screw holes 81 is dependent upon the number of screw holes 81 present. The screw holes 81 originate along the base surface 52 of the shell component 80. Each of the screw holes 81 include a beveled counter sink region 82 that enables screws, positioned within the screw holes 81 to lay flush with the base surface 52 of the shell component 80.

Figure 13:
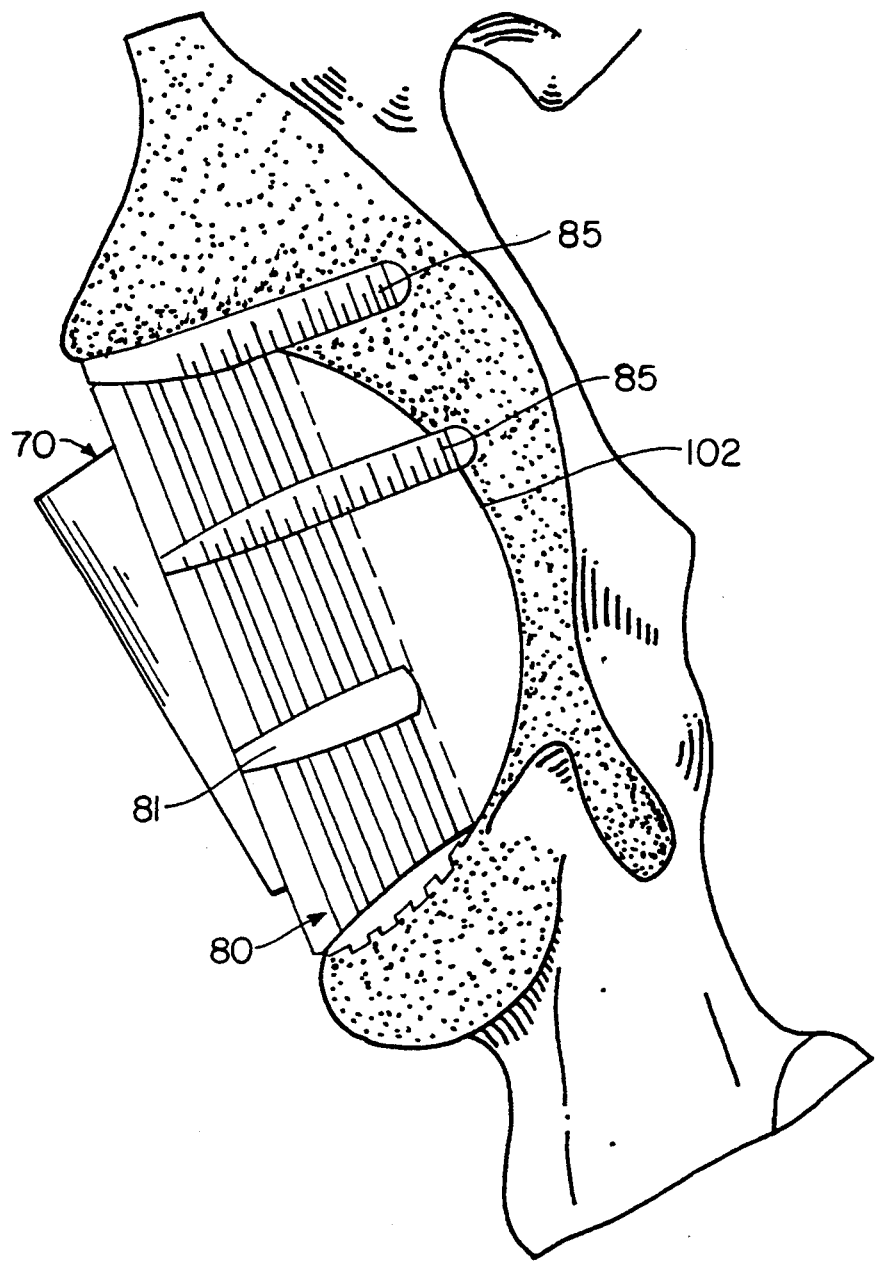
FIG. 13 is a selectively cross-sectioned view of an embodiment of the present invention acetabular cup prosthesis inserted into a prepared acetabulum.

Referring to FIG. 13, the shell component 80 of FIG. 11 and 12 is shown assembled to a bearing insert 70 and positioned in a prepared acetabulum 102. The shell component 80 is originally inserted into the acetabulum 102 in the manner previously described, wherein the shell component 80 is impacted and driven into the acetabulum 102. Once driven into place, the acetabulum 102 is deformed into a shape that conforms to the shape of the shell component 80. Accordingly, under ideal circumstances substantially no gaps occur between the shell component 80 and the acetabulum 102. Screws 85 are then driven through some of the screw holes 81, helping to anchor the shell component 80 to the acetabulum 102.

A plurality of screw holes 81 are symmetrically disposed on the shell component 80. However, when the shell component 80 is driven into a patient's acetabulum 102, only certain screw holes 81 align with regions of bone capable of safely retaining a screw 85. As such, screws 85 are only place through certain screw holes 81 while other screw holes 81 are left empty. As the number of screw holes 81 present in the shell component 81 increase, so does the probability that multiple screw holes 81 will align above bone capable of safely retaining a screw 85. The empty screw holes 81, are exposed to the bone of the acetabulum 102. Consequently, bone may ingrown into the empty screw hole 81 and help retain the shell component 80 in place.

It will be understood that the acetabular prosthetic described herein is merely exemplary and that a person skilled in the art may make many variations and modifications to the describe embodiment utilizing functionally equivalent components to those described. Furthermore, obvious modifications such as variations in number of locking ribs present on the shell component or the dimensions of the shell component or bearing insert may also be made. All such variations and modifications are intended to be included within the scope of this invention as defined by the appended claims.

What is claimed is:

1. A prosthetic acetabular cup having an outer surface for insertion into a patient's acetabulum, wherein said outer surface includes at least one ellipsoidally shaped region that defines an elliptical plane section having a major axis and a minor axis, wherein said major axis is longer than said minor axis.

2. The acetabular cup according to claim 1, further including an engagement means on said outer surface for mechanically engaging said acetabulum.

3. The acetabular cup according to claim 2, wherein said outer surface defines means for accommodating ingrowth of bone between said outer surface and said acetabulum.

4. The acetabular cup according to claim 2, wherein said outer surface includes an apical region and a rim region, wherein said apical region and said rim region generally conform to an ellipsoidal curvature.

5. The acetabular cup according to claim 4, wherein said engagement means is disposed on said rim region.

6. A prosthetic acetabular cup comprising:
an outer surface for insertion into a patient's acetabulum, said outer surface including an apical region which merges into a rim region, said apical region and said rim region defining an ellipsoid having an elliptical plane section which includes a major axis and a minor axis, wherein said major axis is longer than said minor axis; and
an engagement means disposed on said rim region for mechanically engaging said acetabulum, said engagement means including a plurality of ribs concentrically arranged in parallel on said rim region.

7. A prosthetic acetabular cup comprising:
an outer surface for insertion into a patient's acetabulum, said outer surface including an apical region and a rim region, said apical region and said rim region defining an ellipsoid having an elliptical plane section which includes a major axis and a minor axis, wherein said major axis is longer than said minor axis;

an engagement means disposed on said rim region for mechanically engaging said acetabulum, said engagement means including a plurality of ribs concentrically arranged in parallel on said rim region; and a groove defined between adjacent ones of said ribs on said rim region, said groove having a dovetailed-shaped cross-sectional profile.

8. The acetabular cup according to claim 5, wherein said acetabular cup includes a metallic shell component on which said outer surface is disposed and a plastic bearing insert joined within said shell component with an interference fit.

9. The acetabular cup according to claim 5, wherein a plurality of screw holes are disposed in said metallic shell component, said plurality of screw holes extending through said rim region of said outer surface, whereby said plurality of screw holes are not exposed to said plastic bearing insert.

10. A prosthetic acetabular cup having an outer surface for implantation into a patient's acetabulum that includes at least one groove and a plurality of ribs extending from said outer surface, said at least one groove having a generally dovetailed-shaped cross-sectional profile, said at least one groove having side walls defined by said ribs, whereby bone from said acetabulum can grow within said at least one groove and is mechanically retained by the dovetail shape of said at least one groove, and wherein said outer surface further includes at least one ellipsoidally shaped region that defines an elliptical plane section having a major axis and a minor axis, said major axis being longer than said minor axis.

11. The acetabular cup according to claim 10, wherein said outer surface includes an apical region and a rim region, wherein said ribs and said at least one groove are disposed on said rim region of said outer surface.

12. The acetabular cup according to claim 11, wherein said apical region and said rim region conform to the curvature of an ellipsoid.

13. The acetabular cup according to claim 11, wherein each of said ribs includes an ascending surface that ascends from a horizontal reference plane at an acute angle of inclination and an opposite descending surface that descends from said reference plane at an acute angle of declination.

14. The acetabular cup according to claim 6, wherein each of said plurality of ribs includes a surface that ascends at an acute angle of inclination.

15. The acetabular cup according to claim 14, wherein each of said plurality of ribs includes a surface that descends at an acute angle of declination.

* * * * *